(12) United States Patent
Wiessler et al.

(10) Patent No.: US 9,234,120 B2
(45) Date of Patent: Jan. 12, 2016

(54) METHOD FOR APPLYING A FIRST METAL ONTO A SECOND METAL, AN ISOLATOR OR SEMICONDUCTOR SUBSTRATE, AND THE RESPECTIVE BINDING UNITS

(75) Inventors: Manfred Wiessler, Frankenthal (DE); Peter Lorenz, Dossenheim (DE); Heinz Fleischhacker, Dossenheim (DE); Karola Ursula Fleischhacker, legal representative, Dossenheim (DE); Marlen Fleischhacker, legal representative, Butzbach (DE); Nadja Fleischhacker, legal representative, Dossenheim (DE); Ranjita Ghosh-Moulick, Asanol/W.B. (IN); Sandra Gilles, Aachen (DE); Dirk Mayer, Frechen (DE); Andreas Offenhaeusser, Eynatten (BE)

(73) Assignees: DEUTSCHES KREBSFORSCHUNGSZENTRUM, Heidelberg (DE); FORSCHUNGSZENTRUM JUELICH GMBH, Juelich (DE)

( * ) Notice: Subject to any disclaimer, the term of this patent is extended or adjusted under 35 U.S.C. 154(b) by 0 days.

(21) Appl. No.: 13/813,652

(22) PCT Filed: Aug. 12, 2011

(86) PCT No.: PCT/EP2011/004074
§ 371 (c)(1),
(2), (4) Date: Jul. 10, 2013

(87) PCT Pub. No.: WO2012/019779
PCT Pub. Date: Feb. 16, 2012

(65) Prior Publication Data
US 2013/0319610 A1 Dec. 5, 2013

(30) Foreign Application Priority Data
Aug. 13, 2010 (EP) .................................... 10008481

(51) Int. Cl.
| | | |
|---|---|---|
| C09J 5/00 | (2006.01) |
| C07D 403/04 | (2006.01) |
| C07D 403/12 | (2006.01) |
| C07F 7/18 | (2006.01) |
| H01L 51/00 | (2006.01) |

(52) U.S. Cl.
CPC ............... C09J 5/00 (2013.01); C07D 403/04 (2013.01); C07D 403/12 (2013.01); C07F 7/1836 (2013.01); H01L 51/0022 (2013.01); C07B 2200/11 (2013.01)

(58) Field of Classification Search
CPC .......................................................... C09J 5/00
USPC ........................... 156/326; 544/179; 548/424
See application file for complete search history.

(56) References Cited

U.S. PATENT DOCUMENTS

2010/0016545 A1* 1/2010 Wiessler et al. .............. 530/300

FOREIGN PATENT DOCUMENTS

WO 2007144200 A1 12/2007

OTHER PUBLICATIONS

Kim, E., et al., "Oligosaccharide Mimics Containing Galactose and Fucose Specifically Label Tumour Cell Surfaces and Inhibit Cell Adhesion to Fibronectin", "ChemBioChem", 2005, pp. 422-431, vol. 6.

* cited by examiner

*Primary Examiner* — Daniel Lee
(74) *Attorney, Agent, or Firm* — Hultquist, PLLC; Steven J. Hultquist; Mary B. Grant

(57) ABSTRACT

The present invention concerns a method for applying a first metal onto a second metal, an isolator or semiconductor substrate by a Diels-Alder reaction, in particular a Diels-Alder reaction with inverse electron demand. The present invention further concerns the binding units L 1960 and F 160.

11 Claims, 16 Drawing Sheets

Diels-Alder Reaktion

Dien    Dienophil

Diels-Alder Reaktion with inverse electron demand dienophiles

F348 M

F217 M exo endo dienes

F303

L 1885

F278

F312

F285

METHOD FOR APPLYING A FIRST METAL ONTO A SECOND METAL, AN ISOLATOR OR SEMICONDUCTOR SUBSTRATE, AND THE RESPECTIVE BINDING UNITS

CROSS-REFERENCE TO RELATED APPLICATIONS

This application is a U.S. national phase under the provisions of 35 U.S.C. §371 of International Patent Application No. PCT/EP11/04074 filed Aug. 12, 2011, which in turn claims priority of European Patent Application No. EP10008481 filed Aug. 13, 2010. The disclosures of such international patent application and European priority patent application are hereby incorporated herein by reference in their respective entireties, for all purposes.

The present invention concerns a method for applying a first metal onto a second metal, an isolator or semiconductor substrate by a Diels-Alder reaction, in particular a Diels-Alder reaction with inverse electron demand. The present invention further concerns the binding units L 1960 and F 160.

BACKGROUND ART

Recently, the field of printed electronic application, especially the fabrication of electronic devices based on thin film technology, has drawn immense attention and due to this growing interest, a significant progress has been made in the micro fabrication field using a variety of patterning techniques. Assembling of components for molecular electronics, bioelectronics, and plastic electronics requires gentle lithographic techniques which guarantee the structural and functional integrity of the active building blocks. The so far known disruptive techniques such as evaporation of solids, sputtering, or ion etching generate defective structures in an uncontrolled way (1) (2). Soft lithography techniques (3), based on printing with polymer stamps, are gaining importance since they facilitate the transfer of molecular units and inorganic components at gentle conditions. Several printing approaches have been used so far for transferring metal films/electrodes onto various dielectric or semiconducting material substrates (2) (4) (5) (6) (7) (8). All these techniques require strong adhesion between the substrate and the transferred material. In most cases, however, the adhesion of the starting materials is weak and this may affect the performance of the final device.

Another approach to apply a metal material onto a solid is via linker chemistry. However, the binding chemistry of linker molecules to one solid may interfere with the binding chemistry to the second solid or materials on them. Currently used linker molecules do not provide exclusive binding selectivity for the metal to be transferred. These linker molecules suffer under a lack of versatility to chemically integrate functional (bio-) molecules into electrical (sensing) junctions.

Since the prior art methods are not satisfactory, the present inventors recognized an urgent need to provide a method how metals, preferably group Ib metals such as gold (Au) or copper (Cu), adhere strongly to other metal, isolator or semiconductor surfaces (e.g. $SiO_2$). This method should avoid the generation of defective structures as often recognized with the prior art methods, should be fast and easy to perform and provide high yield products.

In this regard, the inventors have recognized that the surface properties of both the substrate and the metal need to be modified by the introduction of functional groups to overcome the barrier of weak adhesion between the solids and to increase the bonding capacity between them. Surface corrugations have to be compensated in order to provide conformal contact between the solids.

DESCRIPTION OF THE INVENTION

The present invention deals with chemical reactions which promote the adhesion between two solids. The surface properties of both solids are modified by selectively binding complementary functional molecules which are capable to undergo a fast and high yield coupling reaction. Such a fast and high yield coupling reaction is a cycloaddition reaction like the Diels-Alder reaction and especially the variation with inverse electron demand (11), c.f. FIG. 14. Thereby the problem of weak adhesion between the solids can be overcome and the bonding capacity between them is enhanced.

In particular, the present invention concerns a method for applying a first metal onto a second metal, isolator or semiconductor substrate via a Diels-Alder reaction, comprising the following steps:

(a) Building a functional unit 1 by modifying a first metal with a binding unit carrying a diene or dienophile (b) Building a functional unit 2 by modifying a second metal, an isolator or a semiconductor substrate with a binding unit carrying a dienophile or diene, and (c) Reacting the two functional units via their diene and dienophile components, respectively, by a Diels-Alder reaction, thereby binding the first metal to the second metal, isolator or semiconductor substrate surface.

According to the present invention the first or second metal is preferably a group Ib, IVa or VIa metal, such as copper (Cu), silver (Ag), titanium (Ti), chromium (Cr) or gold (Ag).

According to the present invention the isolator substrate is preferably glass or an oxide of silicon (Si), germanium (Ge), gallium (Ga) or arsenic (As). Most preferably, the isolator is glass, $Al_2O_3$, $TiO_2$, Ferroelectrics (like $BaTiO_3$, $NaNO_2$, lead titanate ($Pb(Ti)O_3$), lead zirconate titanate ($Pb(Zr_xTi_{1-x})O_3$), lead zirconate, strontium titanate ($Sr_2TiO_3$), barium strontium titanate (($Ba,Sr)TiO3$)) or $SiO_2$.

According to the present invention the semiconductor substrate is preferably a III-V, III-VI, II-VI or IV-IV compound semiconductor like GaP, GaAs, InP, InSb, InAs, GaSb, GaN, AlN, InN, ZnO, ZnS, ZnSe, ZnTe, CdS, CdSe, CdTe, BeSe, BeTe, HgS, GaS, GaSe, GaTe, InS, InSe, SiC or SiGe.

According to the present invention silyl-groups (binds preferably to oxide containing materials like $SiO_x$, $Al_2O_3$, $TiO_2$), cyanates (binds preferably to metals and semiconductors), carboxylic acids (binds preferably to surfaces with positive net charge), sulfides (binds preferably to metals and semiconductors) and disulfides (binds preferably to metals and semiconductors) are preferred binding units.

Between the binding unit and the dien or dienophil a spacer may be present. This is not obligatory but has the advantage of compensating surface roughness, tuning mechanical and electrical properties of molecules. The spacer may be alkyl chains, ethylenglycol chains, allyl chains, polyene, polyine, cyanine, carotene, or benzyl chains.

Thus, a preferred structure is:

Binding-Unit-(Spacer)-Dien or Dienophil

The modification of the first metal on the one side and the second metal, isolator or semiconductor substrate on the other side with the respective binding units carrying the diene or dienophile is carried out according to known methods (12-16). In the following these resulting elements are called "functional units" 1 and 2. The two functional units are:

First metal-Binding unit-(Spacer)-Dien or Dienophil

Second metal/isolator/semiconductor-Binding unit-(Spacer)-Dienophil or Dien

After both functional units are built by carrying either a diene or dienophile they are subjected to react via a Diels-Alder reaction. The Diels-Alder reaction occurs via a single transition state and requires a very little amount of energy to form the final adduct. The entropy of the Diels-Alder reaction is highly negative. The covalent attachment of the diene and the dienophil to a surface accelerates the reaction by lowering the entropy. Since the reactivity of the diene and the dienophiles depends on their structure the velocity of the Diels-Alder reaction with inverse electron demand can be varied. By selecting different pairs of diene/dienophile it is possible to perform two Diels-Alder reactions inverse within the same molecule in a highly specific manner.

The Diels-Alder reaction with inverse electron demand, in contrast to most of the Diels-Alder reactions, is irreversible. In the classical Diels-Alder reaction the diene is carrying electron-releasing and the dienophil is carrying electron-withdrawing groups. In the case of the reversed modus the diene is carrying electron-withdrawing groups or atoms, whereas the dienophile is rich in electrons. Therefore, a double bond in a strained ring system is sufficient as a dienophile. Nitrogen-rich six membered aromatic ring systems like tetrazines are preferably used as dienes. The bicyclic intermediate which is formed during the reaction is stabilized by splitting of nitrogen and the formation of a stable dihydropyrimidine. The splitting of nitrogen is the reason which makes this type of reaction irreversible. The Diels-Alder reaction types are shown in FIG. 14.

It has to be emphasized that the functional units carrying the diene/dienophile is not restricted to the specific surface. E.g. the first metal may carry functional unit having a diene or a dienophile and the metal/isolator/semiconductor substrate may carry the other reaction partner (i.e. dienophile or diene carrying functional unit, respectively). Both functionalities can be used on both. Often only a small modification, i.e. exchange of the binding unit, is needed in the structure to help in surface modification.

The binding units carrying either a diene or a dienophile have binding capability either to the substrate surface (e.g. silicon dioxide) or to the first metal. So the molecules specifically bind to the corresponding surfaces, depending on the binding unit. This is especially advantageous, if a metal layer is printed to a solid substrate surface (e.g. $SiO_2$ surface), on which already metal structures are present. The molecules modifying the solid surface will not affect the metal structures. This is, for example, important for the fabrication of crossbar structures. Mostly it is not wanted that the crossbar electrodes are modified with the adhesion promoting molecules but with other molecules of interest, e.g. redoxactive proteins.

Often it is required that solid surfaces (for instance in molecular electronics) are modified by materials or molecules which perform certain functions like charge storage or current rectification. The modular character of dienes and dienophiles allows to incorporate additional functional groups like redox centers, spacer, magnetizable groups, and many others. Suitable spacers are alkyl chains, ethylenglycol chains, allyl chains, polyene, polyine, cyanine, carotene, or benzyl chains. Suitable redox centers are ferrocene, porphyrins, viologens, aniline and thiophene oligomers, metal transition complexes, carotenes, nitro derivatives of oligophenylene ethynylene, ferrocene, perylene tetracarboxylic bisimide, tetrathiafulvalenes, and fullerene derivatives. Suitable magnetizable groups are metal transition complexes, metal transition complexes with ligands having oxygen e.g. water, hydroxide, alkoxide, alcohol and carboxylate, ferrocene, porphyrins, polymetallic manganese, metal transition complexes with ligands having nitrogen e.g. bipyrimidine, pyrazole, triazole, tetrazole, metal transition complexes with ligands having sulfure e.g. thiolate, and $Mn_{12}$-acetate $EtMe3Sb[Pd(dmit)_2]_2$.

Preferred binding units carrying a diene are L 1960, L 1995, L 2000, F 303, L 1885, F 278, F 312 and F 285 (c.f. FIGS. 1, 15 and 17). In this regard a person skilled in the art would easily recognize that the shown silyl binding units can be easily replaced by cyanates, sulfides or disulfides, depending on the substrate surface properties to which they have to bind.

Preferred binding units carrying a dienophil are F 160, F 545, F 217 M, F 733M or F 348 M (c.f. FIGS. 1, 15 and 16). Also here a person skilled in the art would easily recognize that the shown binding units can be easily replaced by others, i.e. cyanates, sulfides, carboxylic acids or silyl, depending on the substrate surface to which they have to bind.

The binding units L 1960 and F 160 per se are preferred subjects of the present invention.

The synthesis of the dienophilic binding units F 160 and F 545 is shown in FIG. 16. The synthesis of the tetrazines L 1960 and L 1995 is shown in FIG. 17.

In the following the method is described in further detail with regard to a $SiO_2$ substrate as an isolator substrate and a thin film of gold as first metal. This description shall be understood as exemplary preferred embodiment and shall not be construed as any limitation.

The present inventive method enables the transfer of thin film of gold on $SiO_2$ substrate by means of shuttle transfer printing (10) along with chemical modification of both the surfaces. The both surfaces are modified with functional molecules capable to undergo a Diels-Alder reaction with inverse electron demand. The Diels-Alder reaction is basically a cycloaddition reaction that can occur when a conjugated diene is brought in contact with a dienophile and is used as an efficient binding reaction (11). For example, the $SiO_2$ substrate is modified by a synthetic diene and the gold surface is modified with a synthetic dienophile before the printing. After chemical modification, both the surfaces are brought in contact for final irreversible cycloaddition reaction which facilitates the adhesion between metal and $SiO_2$ substrate and helped in printing.

In this particular preferred embodiment where a gold film is applied via a Diels Alder reaction onto a $SiO_2$ substrate the diene and dienophile functional units are preferably L1960 (Mw 583 gilt) and F160 (Mw 492 gilt), respectively. In this regard reference is made to FIG. 1 showing their structural formulas. L1960 has a silane group and is designed especially for the $SiO_2$ surface whereas F160 is designed to have sulfur (S) atoms for binding to the gold substrate.

In this preferred embodiment L1960 is dissolved in an organic solvent, preferably dichloromethane, in a concentration of 0.1 to 0.5 mM, preferably 0.2 0.3 mM, most preferably 0.21 mM. F 160 is dissolved in an alcohol, preferably in methanol or ethanol, with a concentration of 0.5 to 2 mM, preferably about 1 mM.

In this preferred embodiment $Si/SiO_2$ is used with an oxide thickness of 2-10 nm, preferably 3-8 nm, most preferably about 7 nm. Preferably, small pieces of $Si/SiO_2$ cut in 1 cm by 1 cm are used. In this preferred embodiment gold (preferably 10-40 nm, more preferred about 25 nm) is evaporated onto an inert substrate, e.g. glass and further transferred to a polymer stamp. Suitable polymer stamps are polyolefin plastomer (POP) pieces. The gold layer transferred to POP was then further modified with the diene F160.

The invention is further described with regard to the following examples which are not to be construed as limiting the invention. The examples show particular preferred embodiments.

EXAMPLE 1

Surface Reaction

Figure 2:
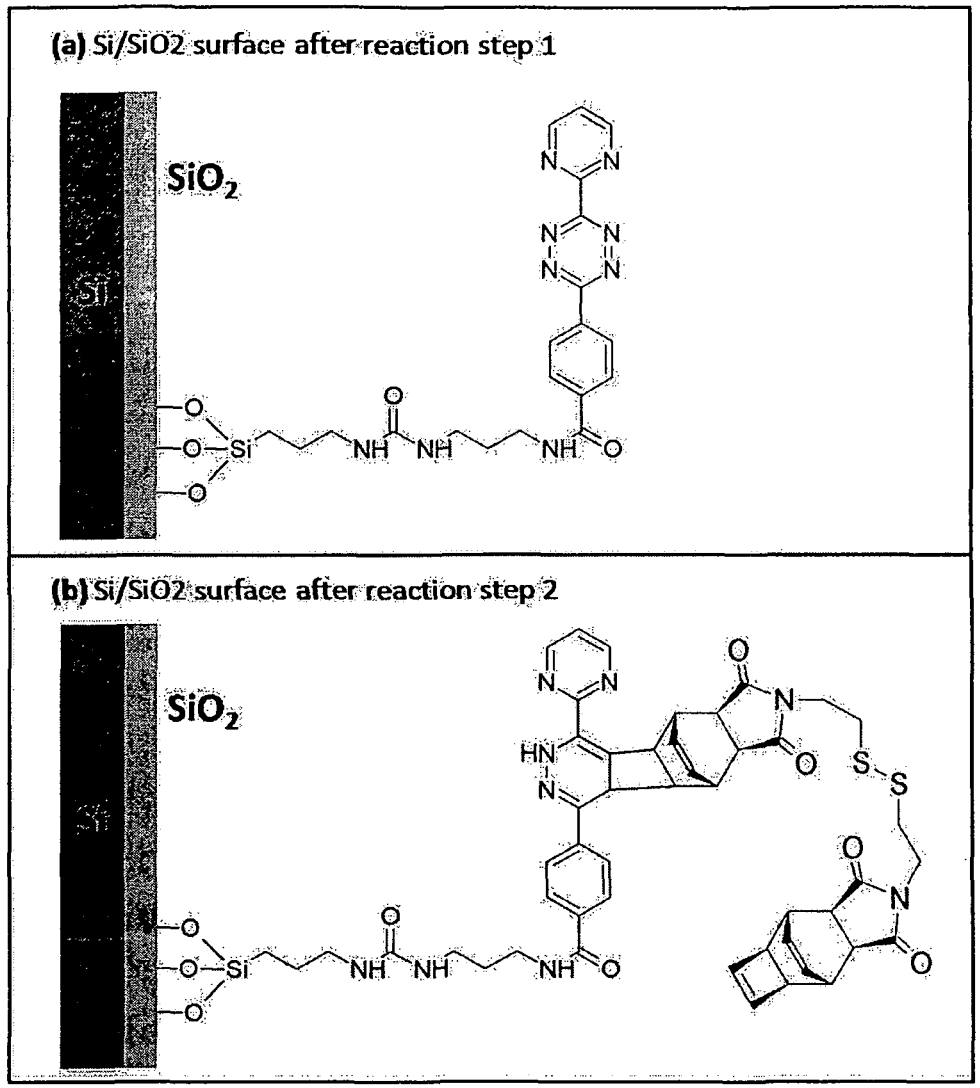
FIG. 2 Schematical view of Diels-Alder reaction on Si/SiO$_2$ substrate, (a) L1960 linked to SiO2 surface via the silane group, (b) F160 linked to L1960 via Diels-Alder reaction

The whole experiment was performed on Si/SiO$_2$ substrate. The cleaning and activation step (reaction step 0) included both wet chemical and plasma cleaning. After removal of the resist the chips were immersed in 2% Hellmanex (Helima, Germany) for 20 min followed by washing with ultra pure water (Milli-Q, Gradient A10 18.2 (MΩ), Millipore Inc., Germany) and drying under Argon. The final activation was done in oxygen plasma (100E Plasma System from Techniques Plasma GmbH, 1.4 mbar, 200 W, 1 min). After activation, the samples were kept in the solution of L1960 overnight with continuous stirring (reaction step 1, FIG. 2a). The next day the samples were removed from the solution of L1960, washed three times with dichloromethane and subsequently immersed in the solution of F160 for final Diels-Alder reaction (reaction step 2, FIG. 2b). This reaction was allowed to go on for 5 hrs. Both steps of the reaction were done at 25° C. After completion of the reaction the substrates were washed with methanol three times and dried.

EXAMPLE 2

Printing

Figure 3:
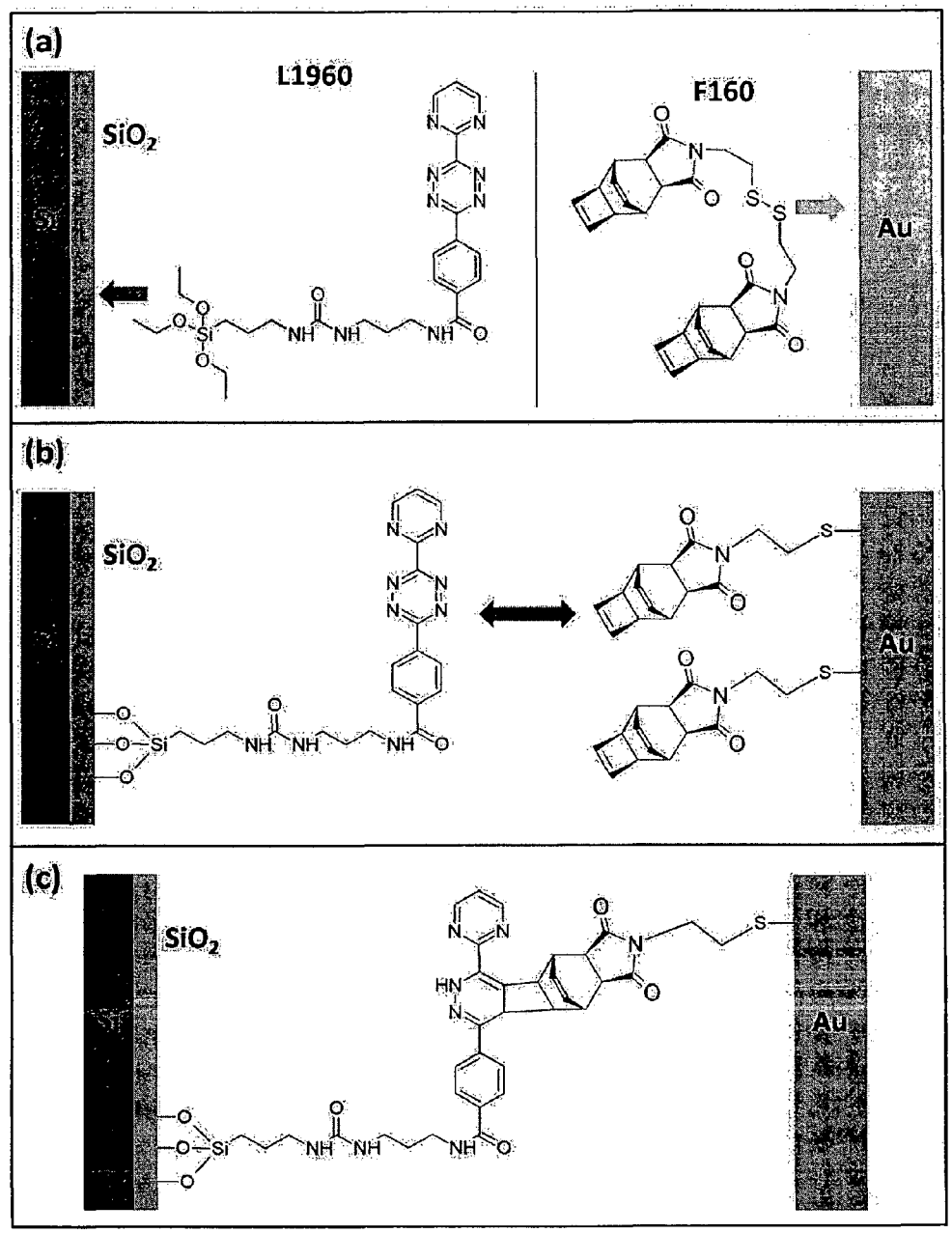
FIG. 3 represents (a) modification of Si/SiO2 substrate with L1960 and of gold with F160 (b) both the modified surfaces before Diels-Alder reaction (c) both the surfaces linked by Diels-Alder reaction
Figure 4:
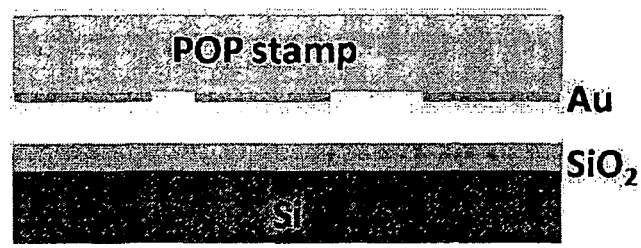
FIG. 4 shows the procedure of shuttle transfer printing FIG. 5 Si 2 p XPS spectra FIG. 6 O 1 s XPS spectra FIG. 7 C 1 s XPS spectra FIG. 8 N 1 s XPS spectra FIG. 9 S 2 s XPS spectra FIG. 10 Ellipsometry images of (a) control SiO$_2$ surface, (b) SiO$_2$ surface after binding L1960, (c) SiO$_2$ surface after binding L1960 and F160; scale bars correspond to 100 µm FIG. 11 Optical microscopy images of printed gold layers, scale bars correspond to 400 µm. a) modified Au layer printed onto modified SiO$_2$ sample, b) surface of POP stamp after printing, c) unmodified Au layer after printing onto unmodified SiO$_2$ sample, d) gold layer remaining on surface of POP stamp after printing.
Figure 5:
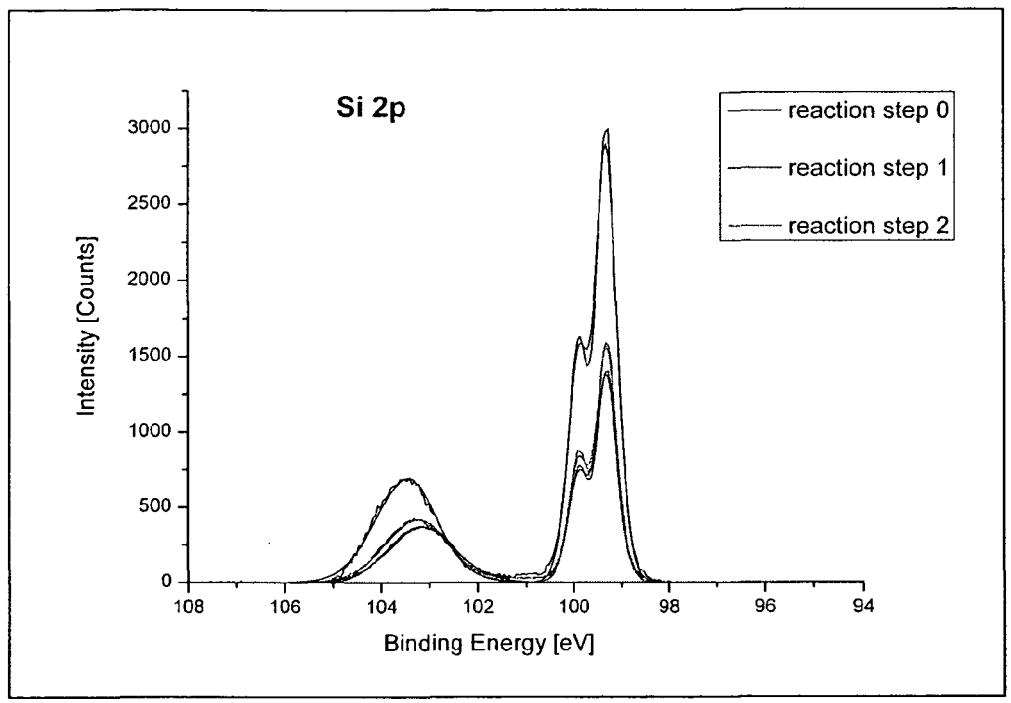
Figure 6:
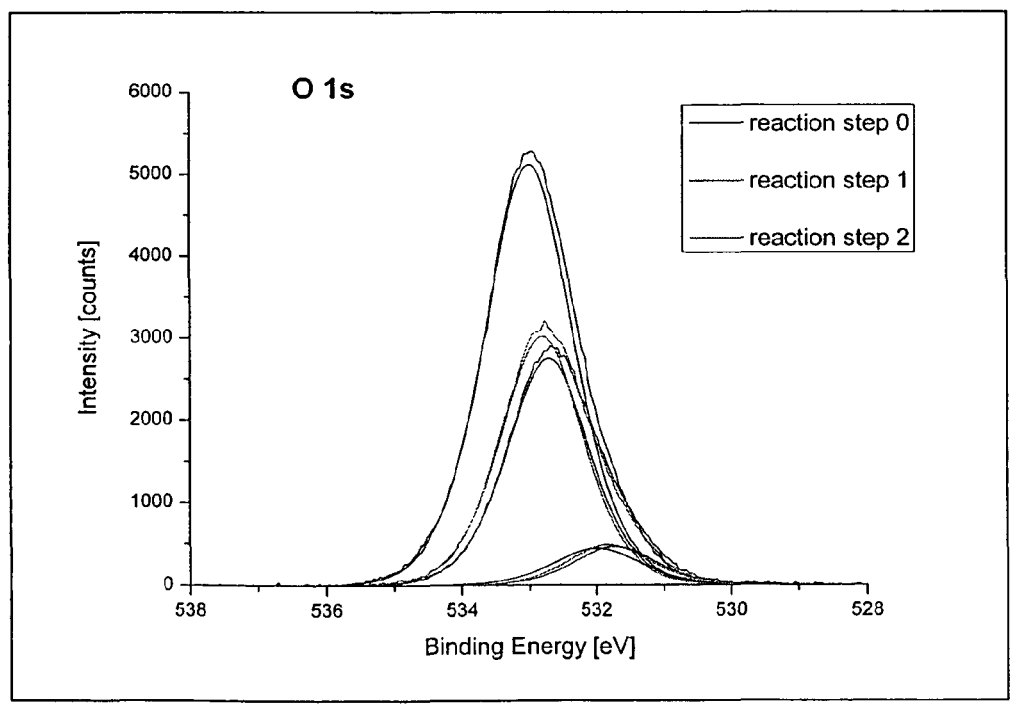
Figure 7:
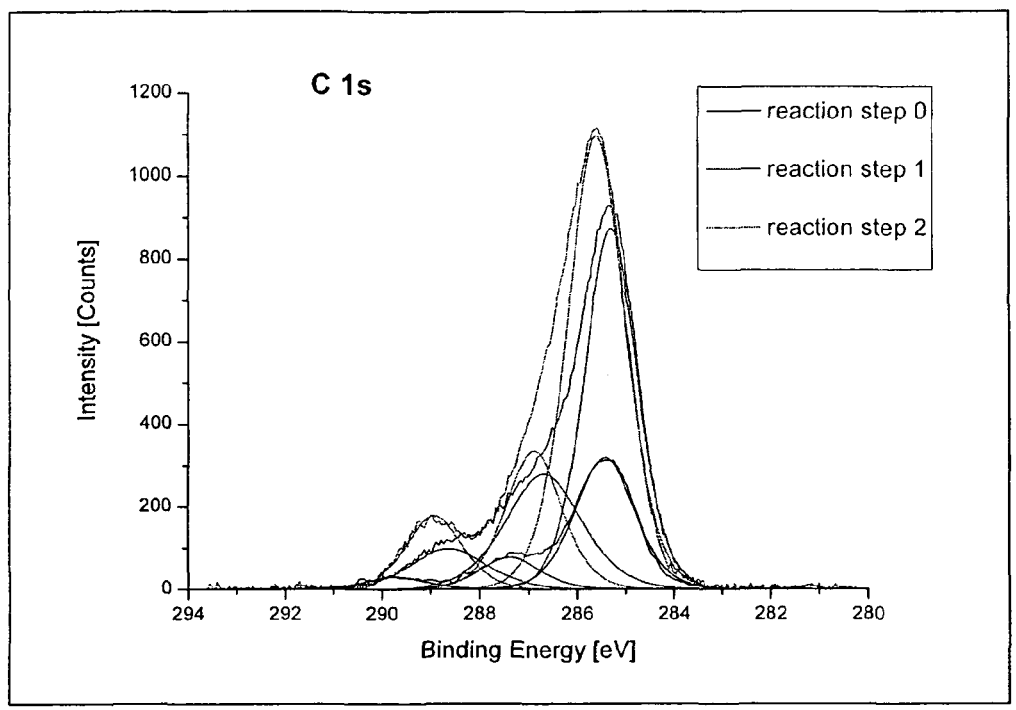
Figure 8:
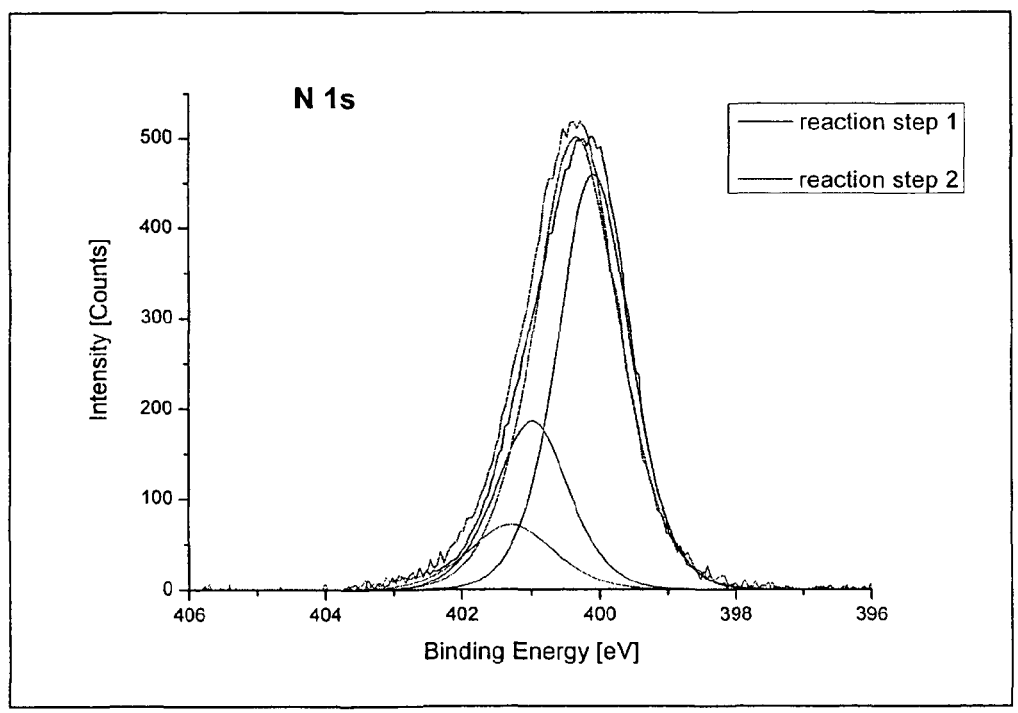
Figure 9:
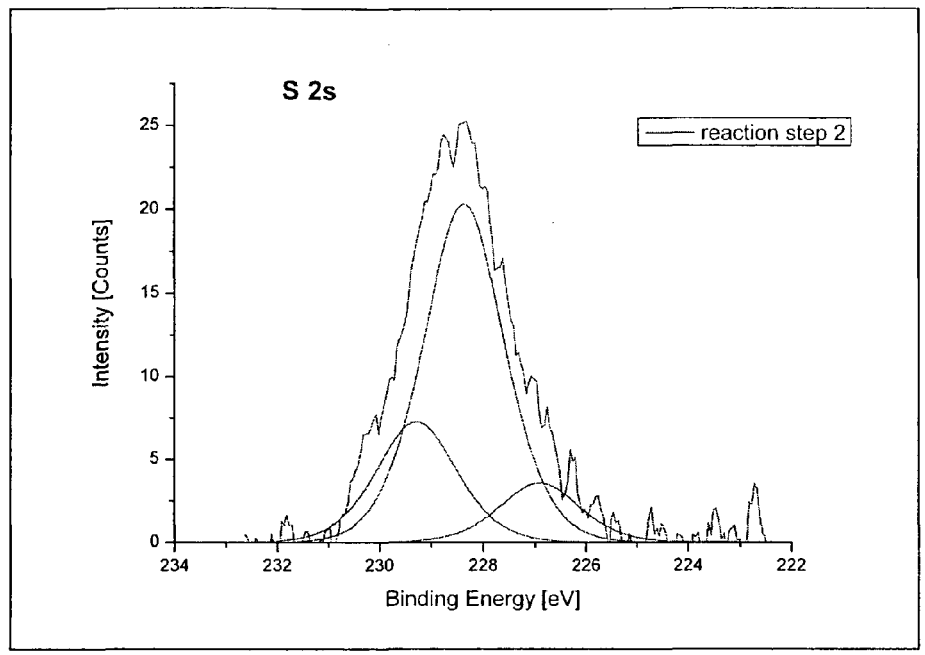

As in example 1, the Si/SiO$_2$ surface was modified with L1960 (FIG. 3a, left hand side) using the same conditions and after washing with dichloromethane it was dried. On the other hand, the gold layer on a POP stamp was modified with F160 (FIG. 3a, right hand side) for 5 hrs at 25° C. After the reaction with F160, the POP substrate containing the modified gold layer was washed with methanol and brought in contact with the modified Si/SiO$_2$ (FIG. 3b). The final printing of the gold layer on this modified Si/SiO$_2$ substrate was done using the principle of shuttle transfer printing as shown in the schematics of FIG. 4. Si/SiO$_2$ substrate and gold containing POP stamp were kept in contact overnight, allowing the Diels-Alder reaction to occur (FIG. 3c).

Additionally the shuttle transfer printing process was done with a modified gold layer on an unmodified silicon dioxide substrate. The reaction conditions for this control sample were the same as described before.

EXAMPLE 3

Process Characterization

The surface reaction of example 1 was investigated by XPS (example 3a) and ellipsometry (example 3b), whereas printing (example 2) was investigated using optical microscopy (example 3c) and TOF-SIMS (example 3d).

EXAMPLE 3a

X-Ray Photoelectron Spectroscopy (XPS)

The surface reactions described in example 1 were monitored by x-ray photoelectron spectroscopy (XPS) and the results are summarized in Table 1.

TABLE 1

| Reaction step | Element | Binding energy [eV] | Relative concentration [atom %] | Σ Relative concentration [atom %] | Chemical assignment |
|---|---|---|---|---|---|
| 0 | Si 2p | 103.3 | 13.8 | 43.6 | Si, SiO$_2$ |
|   |       | 99.3  | 29.8 |      |   |
| 1 |       | 103.0 | 9.8  | 27.0 |   |
|   |       | 99.3  | 17.2 |      |   |
| 2 |       | 103.1 | 9.4  | 26.1 |   |
|   |       | 99.3  | 16.7 |      |   |
| 0 | O 1s  | 533.0 | 43.6 | 47.4 | SiO$_2$ |
|   |       | 532.0 | 3.8  |      |   |
| 1 |       | 532.7 | 27.2 | 31.8 | SiO$_2$, Organic O |
|   |       | 531.7 | 4.6  |      |   |
| 2 |       | 532.8 | 26.2 | 30.4 |   |
|   |       | 531.8 | 4.2  |      |   |
| 0 | C 1s  | 289.7 | 0.6  | 8.9  | Organic contamination |
|   |       | 287.4 | 1.6  |      |   |
|   |       | 285.4 | 6.7  |      |   |
| 1 |       | 288.6 | 3.3  | 32.6 | C=O |
|   |       | 286.7 | 9.2  |      | C—N |
|   |       | 285.3 | 20.1 |      | C—C |

TABLE 1-continued

| Reaction step | Element | Binding energy [eV] | Relative concentration [atom %] | Σ Relative concentration [atom %] | Chemical assignment |
|---|---|---|---|---|---|
| 2 | | 288.9 | 3.8 | 35.0 | C=O |
| | | 286.9 | 7.2 | | C—N |
| | | 285.6 | 24.0 | | C—C |
| 0 | N 1s | | | | |
| 1 | | 401.0 | 2.5 | 8.7 | Ring-N |
| | | 400.1 | 6.2 | | CO—NH |
| 2 | | 401.3 | 1.0 | 7.8 | Ring-N |
| | | 400.3 | 6.8 | | CO—NH |
| 0 | S 2s | | | | |
| 1 | | | | | |
| 2 | | 229.3 | 0.2 | 0.8 | S—S |
| | | 228.4 | 0.5 | | |
| | | 226.9 | 0.1 | | |

When possible, the signals were assigned to specific atoms (chemical assignment). The corresponding spectra are shown in FIGS. 5 to 9. Measurements were done on the bare silicon dioxide surface (reaction step 0), after coupling L1960 (reaction step 1) and after coupling F160 (reaction step 2).

The silicon (FIG. 5) and oxygen (FIG. 6) signals show a decrease after binding the organic molecules in comparison to the bare $SiO_2$ surface. This agrees with the expectation that the signals originating from the $SiO_2$ background are damped when an additional layer is bound.

The C 1 s signals (FIG. 7) show a clear increasing trend from reaction step 0 to 1 and finally to step 2. That demonstrates the growing amount of carbon on the surface.

Figure 1:
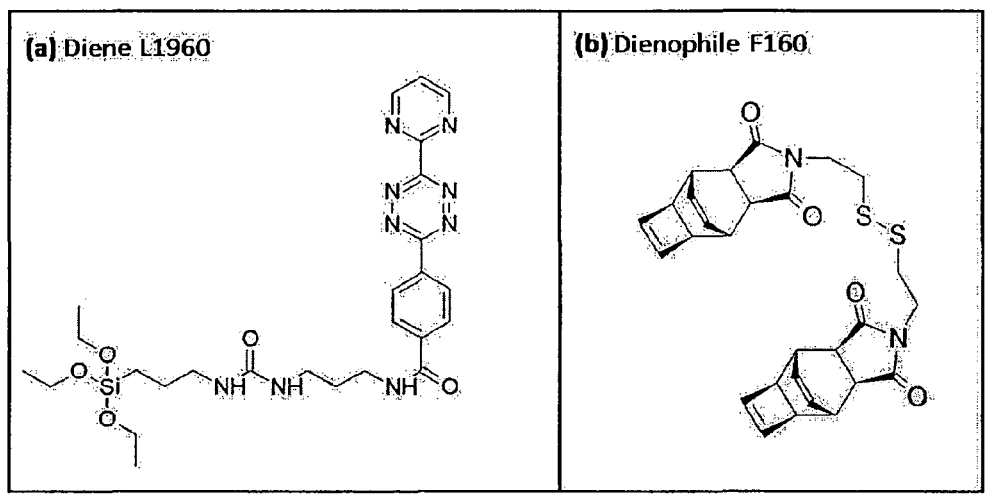
FIG. 1 Chemical structures of (a) L1960 and (b) F160

Nitrogen (FIG. 8) was not found for the bare $SiO_2$ sample, whereas N 1 s signals were detected for the modified surfaces. This corresponds to the presence of several N atoms in the diene and the dienophile molecules (see FIG. 1).

Sulfur (FIG. 9) was only detected for the last sample after the Diels-Alder reaction (reaction step 2). This points out that the sulfur containing F160 bound to the L1960 modified surface.

EXAMPLE 3b

Ellipsometry

The reaction of example 1 was further investigated by ellipsometry. The layer thickness after each reaction step was measured and is recorded in Table 2.

TABLE 2

| Ellipsometric measurements of layer thicknesses | | | |
|---|---|---|---|
| Reaction step | 0 | 1 | 2 |
| Thickness [nm] | 0 | 1.7 | 1.2 |

After binding L1960 to the surface (reaction step 1) the layer thickness amounts to 1.7 nm. This is in good agreement with the size of the molecules and indicates a dense and full coverage of the surface. After reaction step 2 with F160 the layer thickness decreased to 1.2 nm. The thickness decrease suggests that the first layer was partly removed during the second reaction step. The remaining layer thickness of 1.2 nm shows that there still is an organic layer on the substrate.

Figure 10:
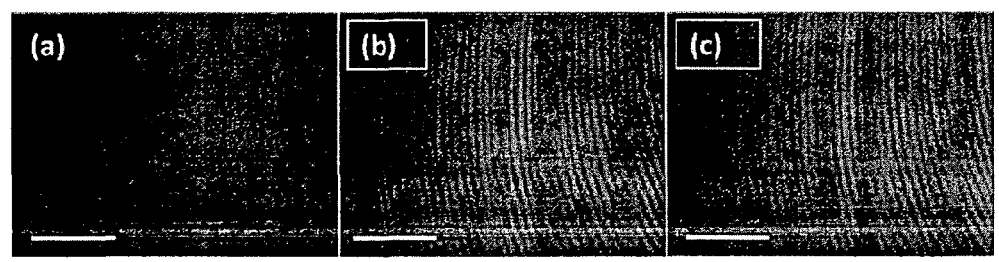

The sample surface was imaged with the ellipsometer before the reaction (FIG. 10a) and after each reaction step (FIG. 10b for reaction step 1 and c for reaction step 2). The surfaces appeared to be clean without significant solid residues of chemicals. This emphasizes that the molecules were bound to the surface as a thin layer and not agglomerated as particles.

EXAMPLE 3c

Optical Microscopy

Figure 11:
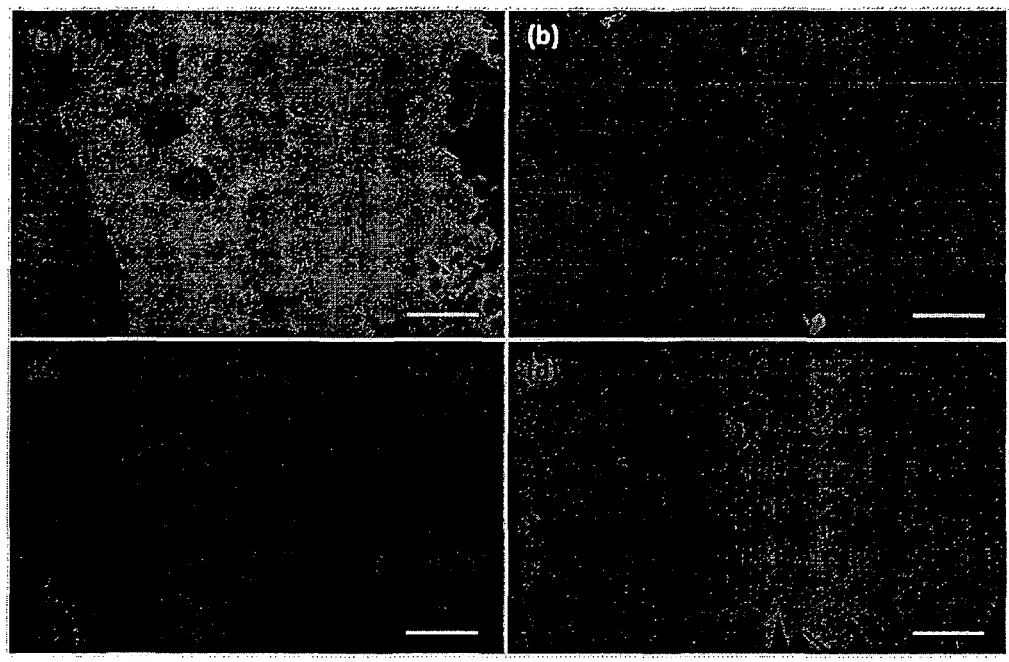

The success of printing a thin gold layer (example 2) was characterized by optical microscopy (FIG. 11).

After pressing a F160 modified gold layer on L1960 modified $SiO_2$ surface and removing the POP shuttle stamp, the gold layer was almost completely transferred to the $SiO_2$ surface (FIG. 11a). Only minor residues remained on the POP surface (FIG. 11b). As control a F160 modified gold layer was pressed on an unmodified $SiO_2$ surface. After removing the POP shuttle, almost no gold was transferred to the $SiO_2$ surface (FIG. 11c). The gold layer remained almost completely on the POP stamp (FIG. 11d).

That demonstrates that the chemical modification enhanced significantly the adhesion between gold and silicon dioxide surface to facilitate the successful transfer from the polymer stamp.

EXAMPLE 3d

TOF-SIMS

Figure 12:
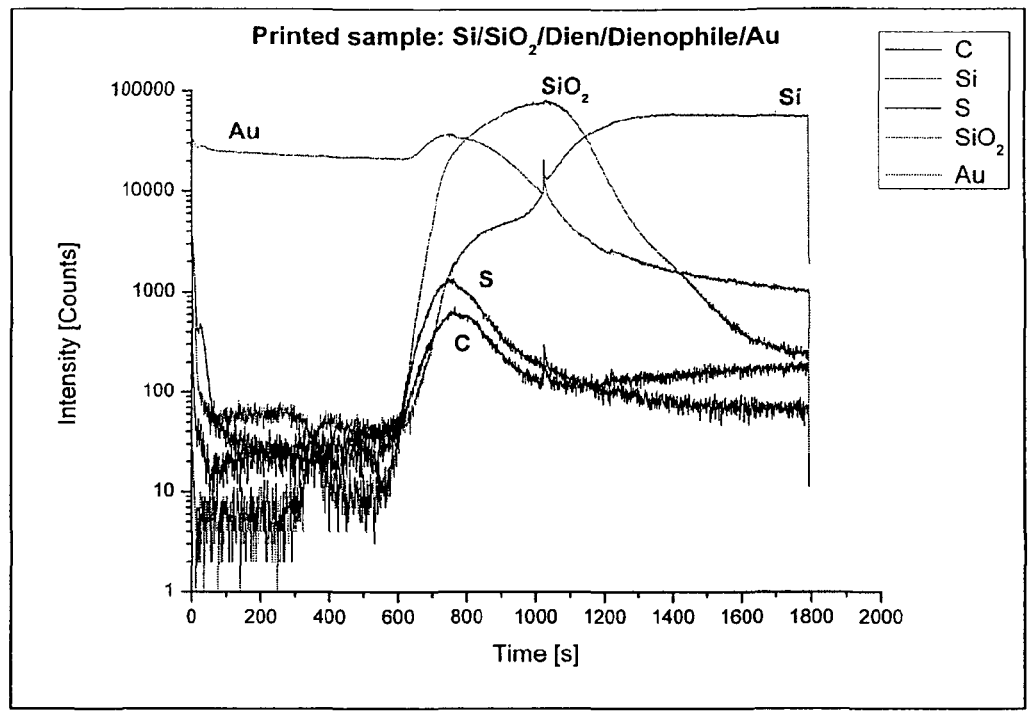
FIG. 12 ToF-SIMS measurement of printed sample

The successfully printed gold layer on $Si/SiO_2$ substrate with diene and dienophile therein between as adhesion promoter was further investigated by time of flight secondary ion mass spectrometry (TOF-SIMS) (FIG. 12). First a high amount of gold is detected, which decreases with an increase of the silicon signal. In between a rise and fall of the silicon dioxide signal, present at the silicon surface, is detected. At the border between Au and $SiO_2$, peaks originating from sulfur and carbon are found, indicating the presence of organic diene and dienophile.

Figure 13:
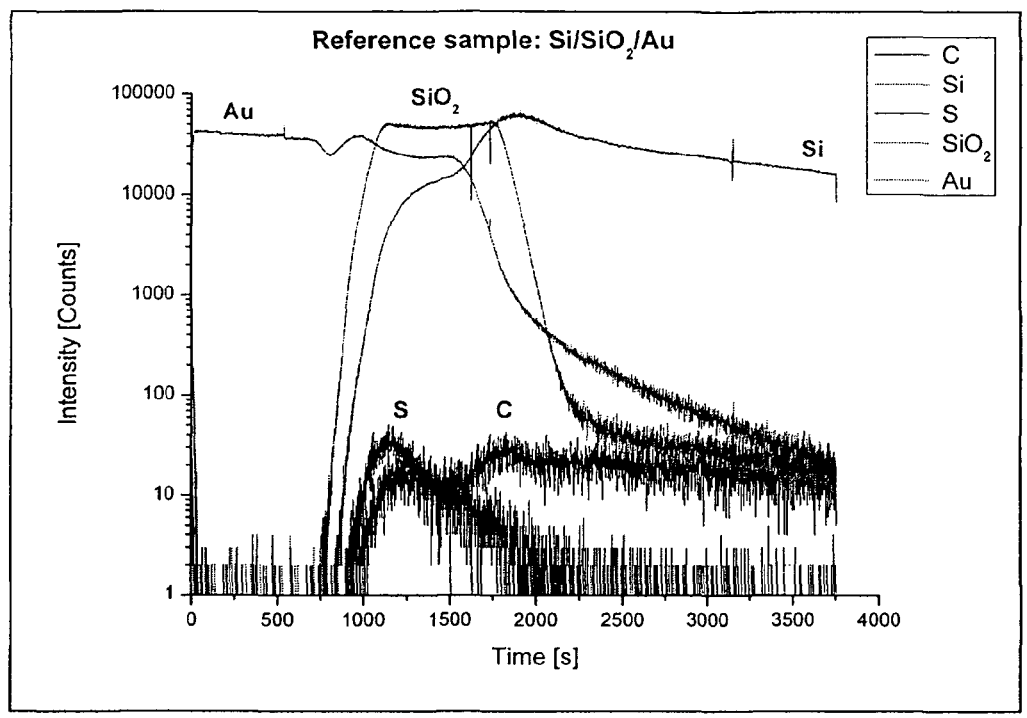
FIG. 13 ToF-SIMS measurement of reference sample
Figure 14:
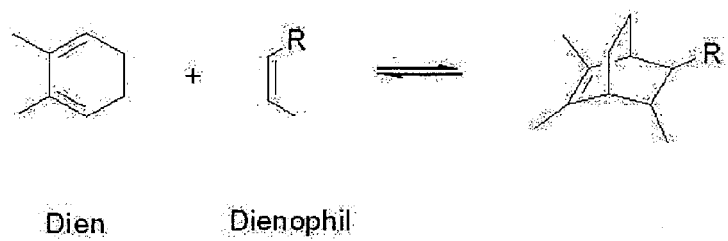
FIG. 14: General Schemes of Diels-Alder reaction and Diels-Alder reaction with inverse electron demand
Figure 14:
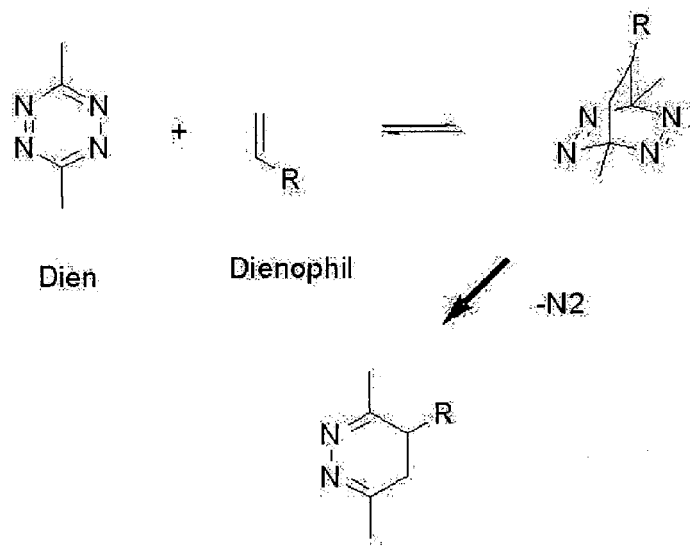
Figure 15:
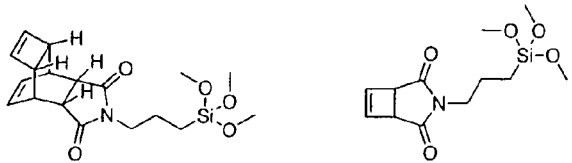
FIG. 15: Diene/Dienophile carrying functional units
Figure 15:
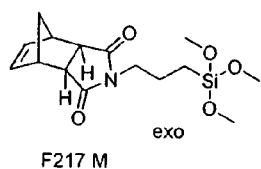
Figure 15:
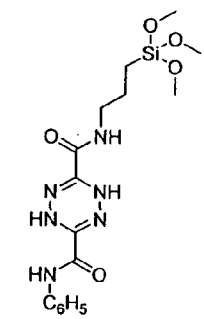
Figure 15:
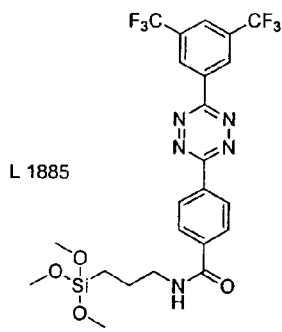
Figure 15:
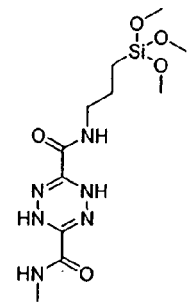
Figure 15:
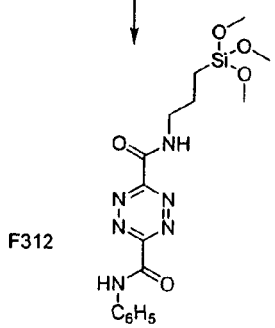
Figure 15:
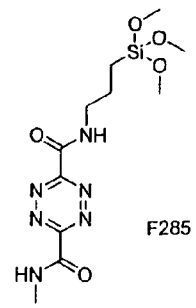

As control a $Si/SiO_2$ sample was coated with a thin evaporated gold layer without any adhesion layer in between and investigated by TOF-SIMS (FIG. 13). The signals of Au, $SiO_2$ and Si appear similar as for the printed sample. Sulfur and carbon are also found here, probably due to contamination. The level of S and C of the printed sample is significantly higher (one to two orders of magnitude) than detected for the control sample. This confirms, that the origin of these signals is the artificial adhesion layer and not contamination.

As a conclusion, the process described above is a nice solution of printing metal on oxide surfaces, by conducting simple organic chemical reaction between the two surfaces. By modifying the molecules fast bonding, high yield, surface roughness compensation, exclusive binding selectivity, and versatile coupling capabilities of functional molecules can be realized.

EXAMPLE 4

Figure 16:
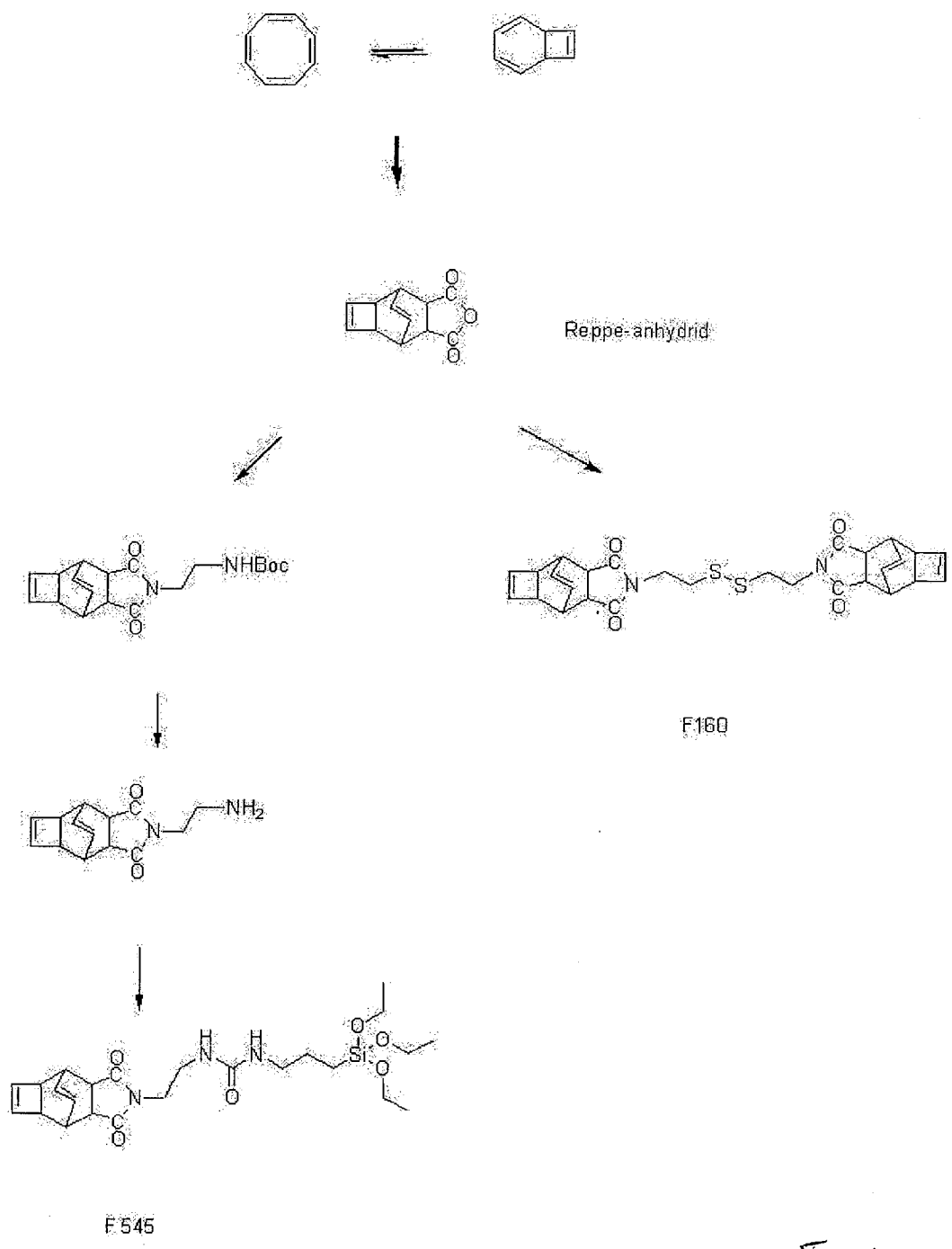
FIG. 16: Synthesis of the binding units carrying a dienophile F160 and F545

Synthesis of the Dienophilic Binding Units F 160 and F 545 (FIG. 16)

For the synthesis of F 160 cystamine hydrochloride is given into methanol and an amine is obtained by the addition of an equivalent amount of triethylamin. After the addition of two equivalents of the Reppe anhydride the mixture is heated for 6 hours under reflux. After cooling down to room temperature the product is obtained and can be recrystallized from ethyl acetate. For the synthesis of F 545 the Reppe anhydride is heated with an equivalent amount of mono-boc-1,2-diaminoethane in ethanol for 6 hours under reflux. The imide crystallizes already when cooling down. Recrystallisation is made from di-isopropylether. The obtained product is dissolved in DCM for removing the protecting Boc-group and the same amount of TFA is added. After 12 hours the solution is narrowed down and diethylether is added. Crystallisation occurs. The amine is obtained as a triflat and can be directly used. The reaction with 3-(tri-ethoxysilyl)-propylisocyanate in the presence of one equivalent Hünig Base (ethyl diisopropylamine) provides the desired product. After purification via column chromatography the urea compound is obtained as a solid (Yield: 80%).

EXAMPLE 5

Figure 17:
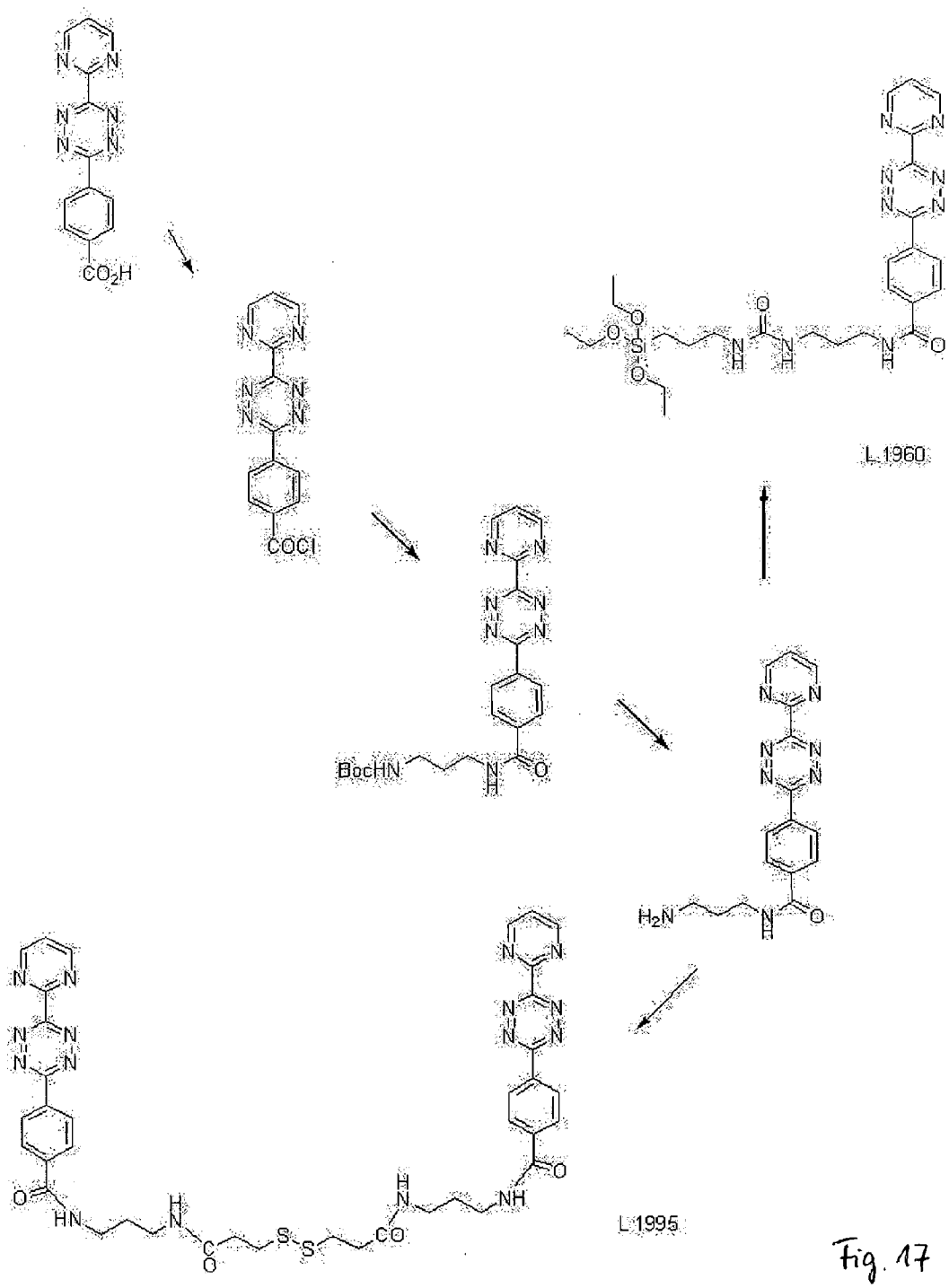
FIG. 17: Synthesis of the binding units carrying a diene L 1960 and L 1995

Synthesis of the Dienic Binding Units L 1960 and L 1995 (FIG. 17)

Tetrazine monocarboxylic acid (c.f. PCT/EP2007/005361) is reacted with thionyl chloride to obtain the respective acid chloride which is reacted with mono-boc-1,3 di-amino propane in the presence of Hünig Base. The amide is obtained after recrystallization from acetone with a good yield. The cleavage of the boc-group is carried out with trifluoroacetic acid (TFA) in DCM. The trifluoromethanesulfonic acid (triflat) of the amine is obtained in crystalline form and can be directly used. The reaction of this compound with 3-(triethoxysilyl)-propylisocyanate in the presence of Hünig Base provides the urea compound L 1960. After purification by column chromatography the silyl compound is obtained as a solid.

The reaction of 2 equivalents of the "triflat" with 1 equivalent di-acid chloride of dithiodipropionic acid (obtained by the reaction of the acid with thionyl chloride) provides the tetrazine disulfide L 1995. The purification is made after column chromatography by recrystallization from acetone. Yield: 50-70%

EXAMPLE 6

Figure 18:
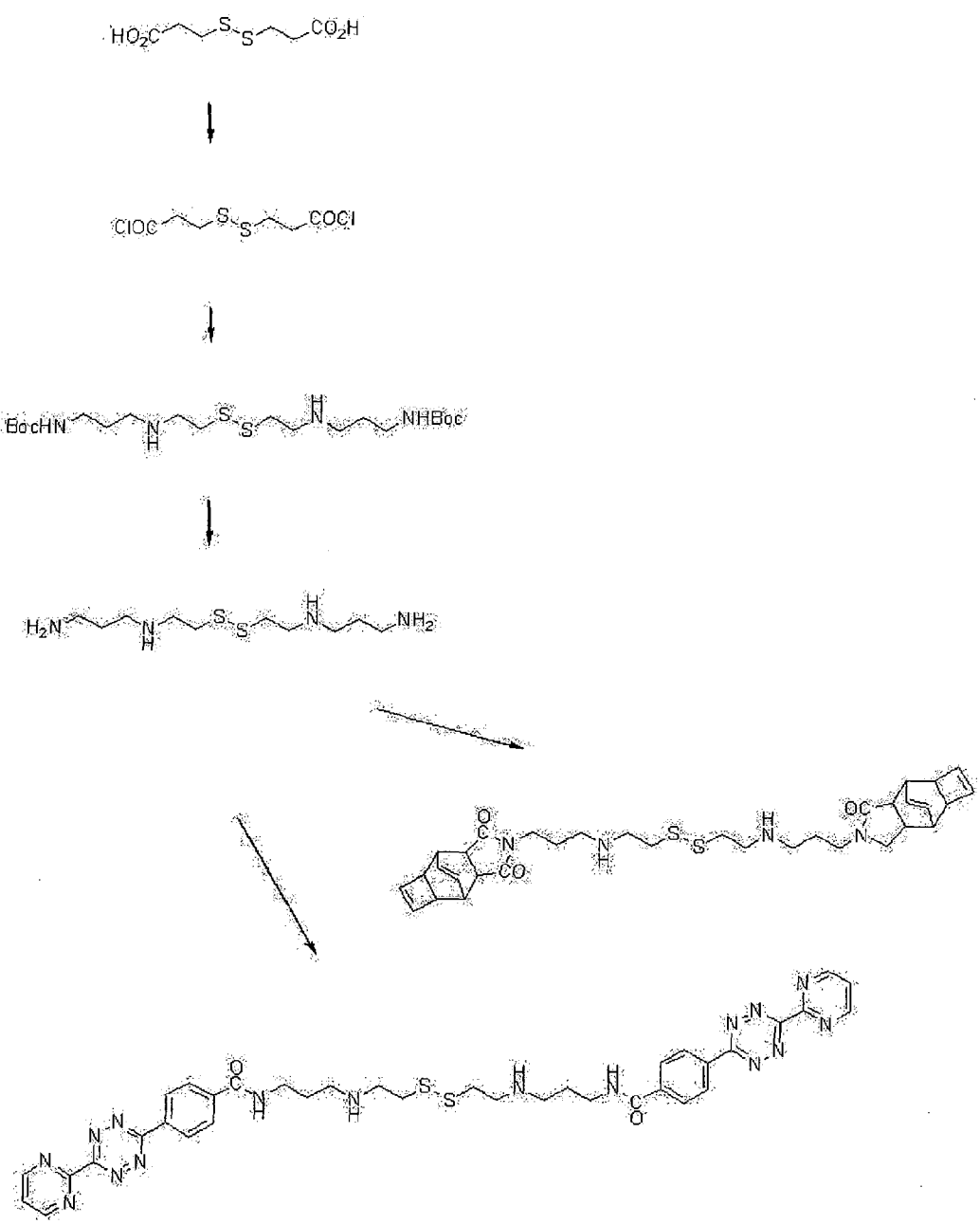
FIG. 18: Synthesis of the diamides of di-thio propionic acid

Synthesis of the Diamides of Dithio-Dipropionic Acid (FIG. 18)

This synthesis is an alternative to obtain binding units with a disulfide bridge. The acid dichloride of dithio-dipropionic acid is obtained by reacting dithio-dipropionic acid with oxalylchloride in DMF/acetonitrile. This compound is reacted in-situ with mono-boc protected diamines. The thus obtained diamides are purified by recrystallization.

These diamides are then reacted with TFA in dichloromethane and the respective diamines are obtained as "triflats". These are stirred with aqueous sodium carbonate solution to obtain the free amines.

If the diamine is reacted with a double amount of Reppe anhydride in ethanol under conditions known in the art, the diimide is obtained in a satisfactory amount. The purification is made by recrystallization. The mass spectrum and 1H-NMR confirm the structures.

By using this synthesis concept a number of dienes and dienophiles can be coupled to the disulfide compound. The reaction of the diamine with the Reppe anhydride (FIG. 16) provides the disulfide F 737 with a good yield. The reaction with the tetrazine acid chloride (FIG. 17) provides the respective tetrazine disulfide.

EXAMPLE 7

Figure 19:
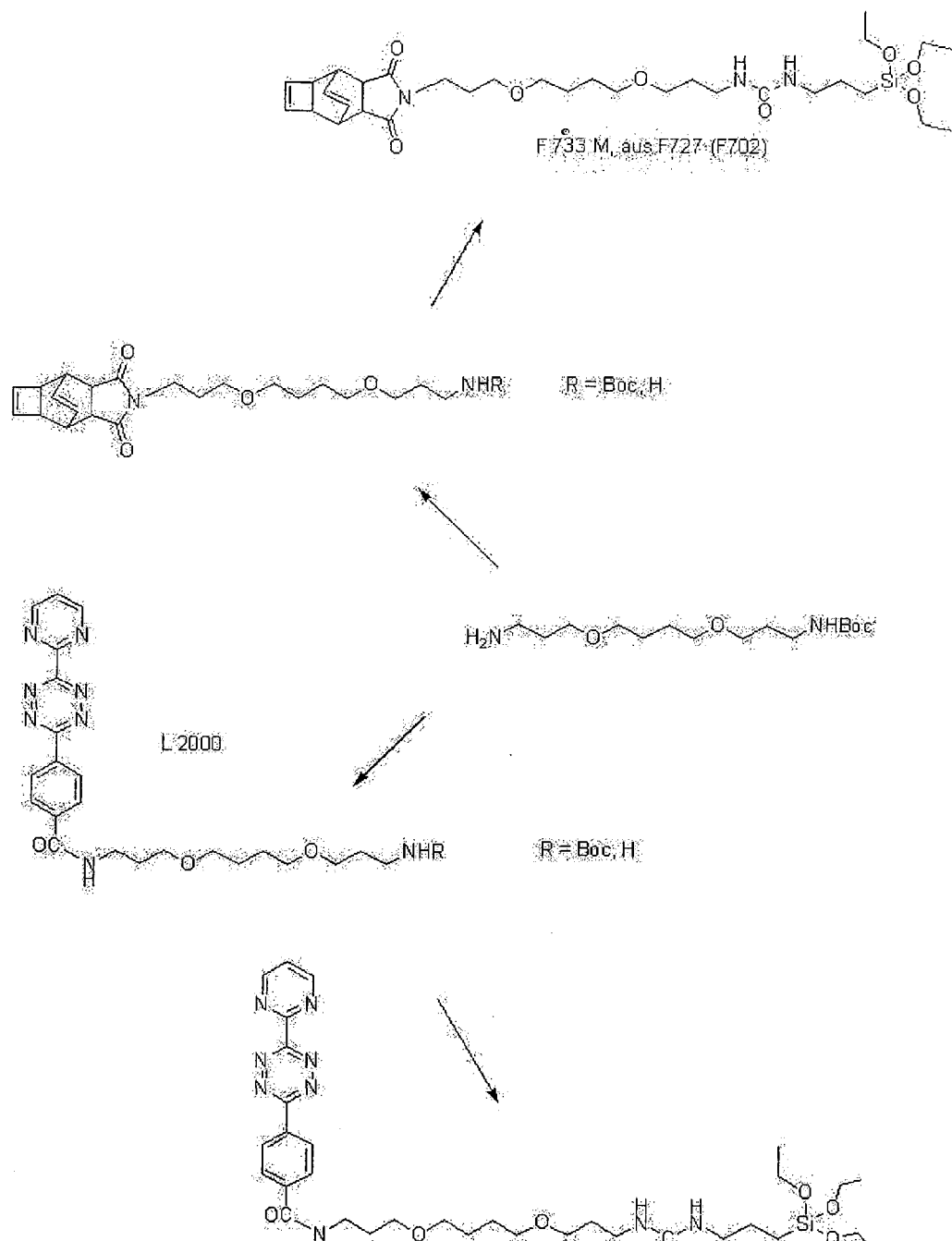
FIG. 19: Synthesis of the silyl compounds

General Method for the Synthesis of Silyl Compounds (FIG. 19)

Reacting the respective mono-boc protected diamine (e.g. 1,4-bis-(3-aminopropyloxy)-butan) with 3-(triethoxysilyl)-propylisocyanate in the presence of Hünig Base provides the respective silyl compounds as shown in FIG. 19.

LITERATURE

1. Loo, Y.-L., et al. 2003, NSF Workshop; University of Rochester
2. Loo, Y.-L., et al. 2003, Nano Letters, Vol. 3, pp. 913-17.
3. Xia, Y. and Whitesides, G. M. 1998, Annu. Rev. Mater. Sci., Vol. 28, pp. 153-84.
4. Hur, S.-H., et al. 2004, Applied Physics Letters, Vol. 85, pp. 5730-32.
5. Loo, Y.-L., et al. 2002, Applied Physics Letters, Vol. 81, pp. 562-64.
6. Menard, E., et al. 2004, Langmuir, Vol. 20, pp. 6871-78.
7. Ojima, K., et al. 2005, Applied Physics Letters, Bd. 87, S. 234110.
8. Hines, D. R., et al. 2005, Applied Physics Letters, Vol. 86, p. 163101.
9. Wöll, C. 2007, Progress in Surface Science, Vol 82, pp 55-120
10. Schwaab, D. Dissertation, RWTH Aachen. 2007. ISSN 0944-2952.
11. Kim, E. Y.-L., et al. 2005, ChemBioChem, Bd. 6, S. 422-31
12. Plueddemann, E. P. Silane coupling agents. Plenum Press, 1982
13. Onclin, S.; Ravoo, B. J.; Reinhoudt, D. N. Angewandte Chemie, 117:6438, 2005,
14. Allara, D. L.; Parikh, A. N.; Rondelez, F. Langmuir, 11(7):2357, 1995.
15. Angst, D. L.; Simmons, G. W. Langmuir, 7:2236, 1991.
16. Schreiber F. Progress in Surface Science 65 (2000) 151-256

The invention claimed is:

1. A method for selectively printing a metal layer to a solid substrate via a Diels-Alder reaction with inverse electron demand, comprising the following steps: (a) forming a metal layer on an inert substrate; (b) building a functional unit 1 by modifying the metal layer with a binding unit carrying a diene or dienophile; (c) building a functional unit 2 by modifying a solid substrate with a binding unit carrying a dienophile or diene; and (d) reacting the two functional units via their diene and dienophile components, respectively, by a Diels-Alder reaction with inverse electron demand, thereby printing the metal layer to the solid substrate surface.

2. The method of claim 1, wherein the metal comprises a group Ib, IVa or VIa metal.

3. The method of claim 1, wherein the metal layer comprises copper (Cu), silver (Ag) or Gold (Au).

4. The method of claim 1, wherein the solid substrate comprises glass or an oxide of silicon (Si), germanium (Ge), gallium (Ga) or arsenic (As).

5. The method of claim 1, wherein the solid substrate is a semiconductor substrate comprising a III-V, III-VI, II-VI or IV-IV compound semiconductor.

6. The method of claim 1, wherein either one of or both of the binding units are a silyl-group, cyanate, sulfide or disulfide.

7. The method of claim 1, wherein a spacer is present between either one of or both of the binding units and the diene or dienophile.

8. The method of claim 1, wherein in step (b) and (c), respectively, the following functional units are built:

metal layer-Binding unit-optionally spacer-Diene/Dienophile solid substrate-Binding unit-optionally spacer-Dienophile/Diene.

9. The method of claim 1, wherein the binding unit carrying a dienophile is F 160 having the formula

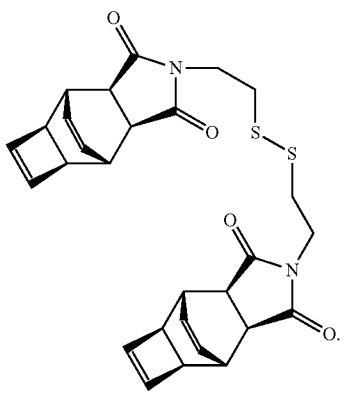 [SMILES: O=C1[C@@H]2[C@@H]3C=C[C@@H]([C@H]4C=C[C@H]43)[C@@H]2C(=O)N1CCSSCCN1C(=O)[C@@H]2[C@@H]3C=C[C@@H]([C@H]4C=C[C@H]43)[C@@H]2C1=O]

10. The method of claim 1, wherein the binding unit carrying a diene is L 1960 having the formula 11. A method for applying a first metal onto a second metal, isolator or semiconductor substrate via a Diels-Alder reaction with inverse electron demand, comprising the following steps:
   (a) building a functional unit 1 by modifying a first metal with a binding unit carrying a diene or dienophile
   (b) building a functional unit 2 by modifying a second metal, an isolator or a semiconductor substrate with a binding unit carrying a dienophile or diene, and
   (c) reacting the two functional units via their diene and dienophile components, respectively, by a Diels-Alder reaction with inverse electron demand, thereby binding the first metal to the second metal, isolator or semiconductor substrate surface, wherein the binding unit carrying a diene is L 1960 having the formula

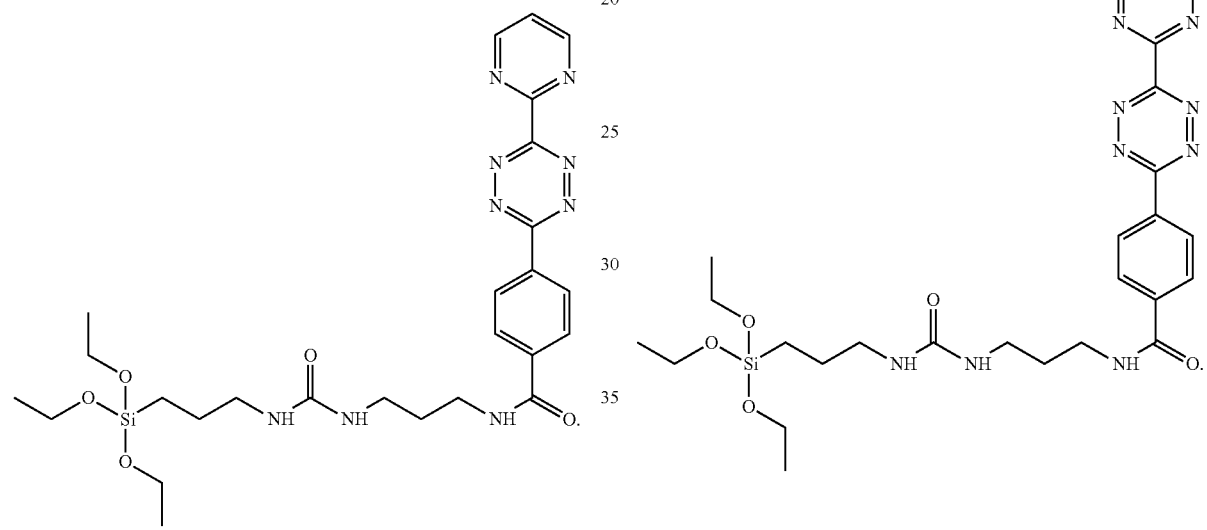

* * * * *